Feb. 8, 1966 G. MERRI Plant Pat. 2,
ACH TREE
Filed Oct. 12,
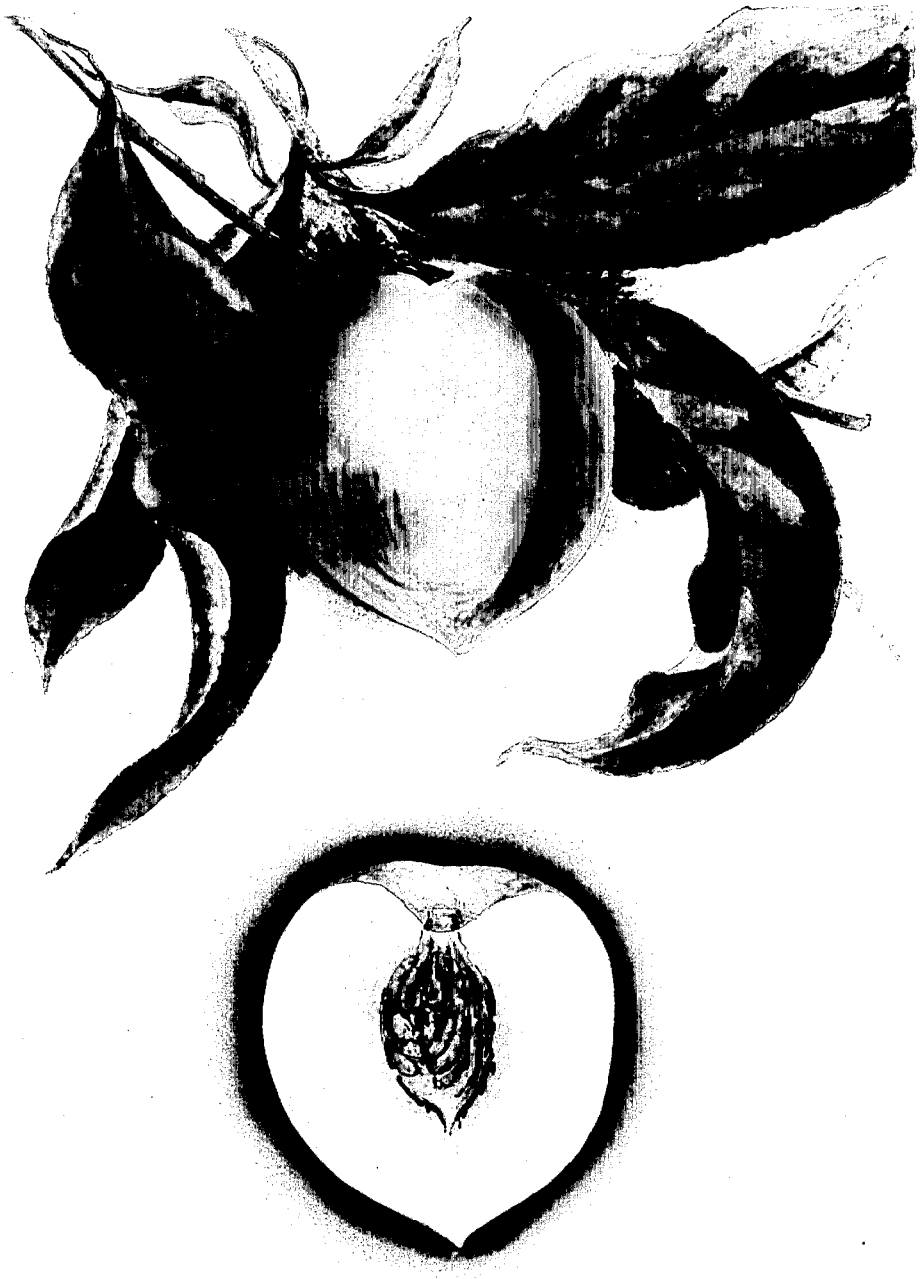
WITNESS
Addison E. Avery
INVENTOR
GRANT MERRILL
Huebner & Worrel
ATTY United States Patent Office Plant Pat. 2,601
Patented Feb. 8, 1966

2,601
PEACH TREE

Grant Merrill, 416 N. Anderson Road, Exeter, Calif.

Filed Oct. 12, 1964, Ser. No. 403,422
1 Claim. (Cl. Plt.—43)

The present invention relates to a peach tree and more particularly to a new and distinct variety thereof broadly characterized by its medium-sized spreading form and its vigorous and heavy bearing of brilliantly red-colored skin, deep yellow-fleshed, finely textured completely freestone peaches having a firm outer flesh area near the skin.

The instant variety blooms early as compared with most other peach varieties at about the same time as the July Elberta peach tree (Plant Patent No. 15). The instant variety is about the same size as the J. H. Hale (unpatented) peach tree. Its fruit ripens at about the same time as the Merrill Gold Rush (unpatented) peach tree, which the instant variety most nearly resembles. The instant variety, however, is distinguished from the Merrill Gold Rush by being somewhat smaller but more spreading and bearing more heavily fruit having more brightly red-colored skin with freestone flesh which is firmer near the skin.

The large peach trees commonly developed for producing peaches for market are, because of their size, difficult economically to prune, thin, and pick. Such large trees have heretofore been regarded as necessary to provide a sufficient crop to support sufficient production per acre to make such operation economically feasible. Furthermore, the peaches produced thereby must be picked at a time prior to full ripening so that the flesh thereof is sufficiently firm to minimize bruising during picking, handling, and shipping. The flavor of such peaches prematurely picked in order to be able to withstand such handling is greatly inferior to peaches which are permitted to remain on the tree until more nearly ripened. Such early picking also adversely affects the skin coloring of the peaches, which impairs their marketability.

Therefore, a primary object of the plant breeding procedures which resulted in the development of this new variety of peach tree was to achieve a completely freestone peach having a firmer outer flesh area near the skin.

Another object was to achieve a peach having a brighter and more attractive skin color.

Another object was to develop a new peach tree of a somewhat smaller, more greatly spreading form.

Another object was to produce a heavier bearing peach tree.

Further objects and advantages will become more fully apparent in the subsequent description in the specification.

I originated the present variety of peach tree on a farm formerly owned by me at Red Bluff, Tehama County, California, in the following manner: Seeds were planted from open pollinated blossoms of the Merrill Gold Rush (unpatented) peach tree. The resultant seedlings were permitted to bear and the fruit carefully examined. The present variety was selected as having outstanding characteristics and was asexually reproduced by grafting to a Merrill June peach tree on a farm formerly owned by me at Lamont, Kern County, California. When the scion came into bearing, the fruit and tree characteristics resulting from such grafting proved identical to those of the original tree.

The accompanying drawing is a water color painting of a characteristic twig of the subject peach tree bearing foliage and a mature fruit and additionally, showing a fruit of the subject variety divided on its suture plane to reveal flesh coloration and pit characteristics.

Referring more specifically to the pomological characteristics of this new and distinct variety of peach tree, the following has been observed under the ecological conditions prevailing at Lamont, Kern County, California, and is an outline description thereof. All major color plate identifications are by reference to Maerz and Paul Dictionary of Color.

*Tree*

Size: Medium, vigorous, spreading, medium dense, vase-shape formed by pruning, and heavy bearer.
Trunk: Medium stocky, medium shaggy.
Branches: Lenticles, numerous in quantity, medium sized.
Leaves: Selected from midportion of vigorous unbranched terminal shoot from 18" to 24" long.
*Size.*—Medium.
*Length.*—6½" to 7½", average 7".
*Width.*—1⅜" to 1⅝", average 1½".
*Form.*—Lanceolate, tip acuminate, medium thin.
*Color.*—Upper surface, medium green (22–L–8); underside, light green (21–J–7); midrib, lighter green (10–I–1).
*Class* (Meader and Blade: Proceedings of Am. Soc. Hor. Sc., vol. 37, page 206)—2. Width-length ratio—average .204. Apex angle—average 18°. Base angle—66° to 73°, average 69½°. Margin—crenate. Petiole—medium long, medium thick. Glands—2 to 6, average 4, opposite and alternate, medium size, reniform.
*Color.*—Mostly green.
*Position.*—On petiole and at base of leaf.
*Stipules.*—At base of leaf, falling off early.
Flower buds: Medium size, truncate to obtuse, plump, free, pubescent.
Flowers: Early, about in season with July Elberta peach tree (Plant Patent No. 15).
*Color.*—Pink.
*Pollen.*—Abundant.

*Fruit*

Maturity when described—firm ripe.

The fruit of the instant variety ripens right after the Red Haven during the first and second weeks in July in Kern County of California and about the second and third weeks of July in Tehama County, California. More specifically, the ripening period for the fruit in Tehama County was from July 15 to July 24 in 1960; from July 10 to July 28 in 1961; and from July 10 to July 18, 1962. In Kern County, the fruit ripened from July 10 to July 18, 1960 and from July 5 to July 16, 1961.

Size: Variable.
*Axial diameter.*—2¾" to 3⅛", average 2 15/16".
*Transverse in suture plane.*—2⅝" to 2⅞", average 2¾".
*At right angles to suture plane.*—2½" to 2¾", average 2⅝".
Form: Variable, generally cordate, some obovate.
*Suture.*—Inconspicuous, extends from base and discontinues at apex. Has slight depression beyond pistil point.
*Ventral surface.*—Lightly lipped on one side.
*Cavity.*—Flaring, rounded to slightly elongated in suture plane. Depth—½" to ⅝", average 9/16"; breadth—½" to ¾", average ⅝". Markings—yellow with some red therein.
*Base.*—Retuse to emarginate.
*Apex.*—Rounded to cuspidate.
*Pistil point.*—Apical.
*Stem.*—Length, averaging ½"; diameter, averaging ⅛"; usually free from stone at maturity, seldom adheres thereto.
Skin: Medium thick, medium tough, tenacious to flesh when firm ripe.

*Tendency to crack.*—None.

*Color.*—Under color—light yellow (11–L–8); over color—moderate red blush (4–L–10) to very dark red blush (7–L–6).

*Down.*—Moderate, short, rolls up moderately when rubbed.

Flesh:

*Color.*—Deep yellow (9–L–6) to (11–L–9) at outer edge with red next to the pit cavity (6–L–6) which occasionally extends into flesh.

*Surface of pit cavity.*—Pink to red.

*Amygdalin.*—Scant.

*Juice.*—Moderate.

*Texture.*—Firm, meaty.

*Fibers.*—Moderate, fine and tender.

*Ripens.*—Evenly.

*Flavor.*—Subacid, mild, sweet.

*Aroma.*—Distinct.

*Eating quality.*—Excellent.

Stone: Completely free.

*Fibers.*—Few and short.

*Size.*—Medium to small.

*Length.*—$1\frac{9}{16}''$ to $1\frac{13}{16}''$; average $1\frac{11}{16}''$.

*Breadth.*—$\frac{3}{4}''$ to $\frac{15}{16}''$; average $\frac{27}{32}''$.

*Thickness.*—$\frac{5}{8}''$ to $\frac{3}{4}''$; average $\frac{11}{16}''$.

*Form.*—Obovate with acuminate tip.

*Base.*—Oblique.

*Hilum.*—Oval.

*Apex.*—Cuspidate.

*Sides.*—Usually equal.

*Surface.*—Irregularly pitted and furrowed more deeply adjacent to the apex end and extended toward the suture edge. Pitted toward base.

*Ventral edge.*—Thick, usually has a deep narrow furrow on each side and a central shallow furrow disappearing toward the tip and apex.

*Dorsal edge.*—Deep furrow, broken at irregular intervals.

*Color.*—Brown to tan (7–H–12) to (8–L–11).

*Tendency to split.*—None.

Use: Market, local, culinary, long-distance shipping.

*Keeping quality.*—Good.

*Resistance to insects and diseases.*—Unknown.

*Shipping quality.*—Good.

Although the new variety of peach tree possesses the described characteristics under the growing conditions in Lamont, Kern County, California, having been first observed near Red Bluff, Tehama County, California, at the northern end of the Sacramento Valley, it is to be understood that variation of the usual magnitude in characteristics incident to the growing conditions, fertilization, pruning and pest control is to be expected.

Having thus described and illustrated my new variety of peach tree, what is claimed as new and desired to be secured by Letters Patent is:

A new and distinct variety of peach tree substantially as illustrated and described and which is characterized by its vigorous growth; its medium size in resemblance to the J. H. Hale (unpatented) peach tree, its spreading form and its regular and heavy bearing of completely freestone, deep yellow-fleshed, finely textured fruit which is substantially firmer in its outer areas near the skin and which most closely resembles the Merrill Gold Rush (unpatented) peach tree from which it is distinguished in its smaller size, greater vigor and productivity and in its bearing of fruit having a more attractive brilliantly red-colored skin with firmer flesh providing greater resistance to bruising.

No references cited.

ABRAHAM G. STONE, *Primary Examiner.*

R. E. BAGWILL, *Assistant Examiner.*